(12) United States Patent
Bettencourt da Silva et al.

(10) Patent No.: US 11,195,119 B2
(45) Date of Patent: Dec. 7, 2021

(54) IDENTIFYING AND VISUALIZING RELATIONSHIPS AND COMMONALITIES AMONGST RECORD ENTITIES

(71) Applicant: International Business Machines Corporation, Armonk, NY (US)

(72) Inventors: Joao H. Bettencourt da Silva, Dublin (IE); Mark B. Hughes, Dublin (IE); Spyros Kotoulas, Dublin (IE); Caroline A. O'Connor, Kilkenny (IE)

(73) Assignee: International Business Machines Corporation, Armonk, NY (US)

( * ) Notice: Subject to any disclaimer, the term of this patent is extended or adjusted under 35 U.S.C. 154(b) by 1009 days.

(21) Appl. No.: 15/862,669

(22) Filed: Jan. 5, 2018

(65) Prior Publication Data

US 2019/0213167 A1 Jul. 11, 2019

(51) Int. Cl.
*G06F 40/30* (2020.01)
*G06N 20/00* (2019.01)
(Continued)

(52) U.S. Cl.
CPC ........... *G06N 20/00* (2019.01); *G06F 16/904* (2019.01); *G06F 40/205* (2020.01);
(Continued)

(58) Field of Classification Search
CPC ..... G06N 20/00; G06F 16/904; G06F 40/279; G06F 40/205; G06F 40/30; G16H 10/60; G16H 50/70; G16H 50/20
See application file for complete search history.

(56) References Cited

U.S. PATENT DOCUMENTS 5,621,876 A * 4/1997 Odam ..................... G06F 40/18
715/212
5,963,670 A 10/1999 Lipson et al.
(Continued)

FOREIGN PATENT DOCUMENTS

CN 101719166 A 6/2010
WO 02096282 A2 12/2002
(Continued)

OTHER PUBLICATIONS

Zhang, Qianqian, Mengdong Chen, and Lianzhong Liu. "A review on entity relation extraction." In 2017 Second International Conference on Mechanical, Control and Computer Engineering (ICMCCE), pp. 178-183. IEEE, 2017. (Year: 2017).*

(Continued)

*Primary Examiner* — Alexey Shmatov
*Assistant Examiner* — Casey R. Garner
(74) *Attorney, Agent, or Firm* — Alexander G. Jochym

(57) ABSTRACT

A capability to identify and visualize relationships and commonalities amongst record entities is provided. A plurality of entities are extracted from one or more records. Each extracted entity is associated with a respective feature vector within a vector space of a feature matrix. The feature vectors are distributed within the feature matrix based on semantic relationships amongst the entities of a corpus. Multidimensional coordinates within a dimensionally-reduced vector space of the feature matrix are generated for each extracted entity. One or more cells of a cellular presentation of the feature matrix are identified such that each identified cell represents one or more respective extracted entities. Each cell represents (i) a respective range of multidimensional coordinates within the dimensionally-reduced vector space of the feature matrix and (ii) one or
(Continued)

more feature vectors of the plurality of feature vectors within the feature matrix.

17 Claims, 7 Drawing Sheets

(51) Int. Cl.
*G06F 16/904* (2019.01)
*G06F 40/205* (2020.01)
*G06F 40/279* (2020.01)
*G16H 10/60* (2018.01)
*G16H 50/70* (2018.01)
*G16H 50/20* (2018.01)

(52) U.S. Cl.
CPC ............ *G06F 40/279* (2020.01); *G06F 40/30* (2020.01); *G16H 10/60* (2018.01); *G16H 50/20* (2018.01); *G16H 50/70* (2018.01)

(56) References Cited

U.S. PATENT DOCUMENTS

| | | |
|---|---|---|
| 6,990,238 B1 | 1/2006 | Saffer et al. |
| 7,010,564 B2 | 3/2006 | Morimoto et al. |
| 8,924,269 B2 | 12/2014 | Seubert et al. |
| 9,535,902 B1 * | 1/2017 | Michalak ................ G06F 40/30 |
| 2004/0027350 A1 | 2/2004 | Kincaid et al. |
| 2004/0080536 A1 | 4/2004 | Yakhini et al. |
| 2006/0135859 A1 | 6/2006 | Iliff |
| 2007/0118399 A1 * | 5/2007 | Avinash ................ G16H 10/60 705/2 |
| 2009/0265188 A1 | 10/2009 | Lamy et al. |
| 2010/0241698 A1 | 9/2010 | Hillerbrand |
| 2010/0251117 A1 | 9/2010 | Baughman et al. |
| 2012/0136679 A1 | 5/2012 | McCafferty |
| 2012/0185792 A1 | 7/2012 | Kimm et al. |
| 2012/0311496 A1 * | 12/2012 | Cao ........................ G06F 16/287 715/821 |
| 2013/0144151 A1 | 6/2013 | Nolte et al. |
| 2015/0040039 A1 * | 2/2015 | Xu ........................ G06F 3/0482 715/762 |
| 2015/0310096 A1 * | 10/2015 | Bao ........................ G06F 16/367 707/738 |
| 2016/0042253 A1 | 2/2016 | Sawhney et al. |
| 2017/0004275 A1 | 1/2017 | Mehta et al. |
| 2017/0161619 A1 * | 6/2017 | Franceschini .......... G06N 5/022 |
| 2019/0278777 A1 * | 9/2019 | Malik ................... G06F 16/367 |
| 2021/0064820 A1 * | 3/2021 | Sorah .................... G06F 40/237 |

FOREIGN PATENT DOCUMENTS

| | | |
|---|---|---|
| WO | 2007131932 A2 | 11/2007 |
| WO | 2016029272 A1 | 3/2016 |
| WO | WO-2019050968 A1 * | 3/2019 ............. G06F 13/38 |

OTHER PUBLICATIONS

Kyan, Matthew, Paisarn Muneesawang, Kambiz Jarrah, and Ling Guan. Unsupervised Learning: A Dynamic Approach. John Wiley & Sons, 2014. (Year: 2014).*

* cited by examiner

400

| Kidney Disease | Sick | Polyphagia (Hunger) | Overweight | Diet |
| Keto-Acidosis | Hyper-glycaemia | Fatigue | Polydipsia (Thirst) | Dehydration |
| Underweight | Type 1 Diabetes | Polyuria | Type 2 Diabetes | Hyper-tension |
| Liver Disease | Insulin MDI | Insulin-Deficiency | Metmorfin | Stress |
| Heart Failure | Tachy | Hypo-Glycaemia | Anxiety | Sweating |

| Sick | Polyphagia (Hunger) | Overweight | Diet |
| Hyperglycaemia | Fatigue | Polydipsia (Thirst) | Dehydration |
| Type 1 Diabetes | Polyuria | Type 2 Diabetes | Hypertension |
| Insulin MDI | Insulin-Deficiency | Metmorfin | Stress |

FIG. 4C

- 422: Sick + Polyphagia + Hyperglycaemia + Fatigue
- 424: Overweight + Diet + Polydipsia + Dehydration
- 426: Type 1 + Polyuria + Insulin MDI + Insulin Deficiency
- 428: Type 2 + Hypertension + Metmorfin + Stress

FIG. 4D

| Overweight | Diet |
| Polydipsia (Thirst) | Dehydration |

IDENTIFYING AND VISUALIZING RELATIONSHIPS AND COMMONALITIES AMONGST RECORD ENTITIES

TECHNICAL FIELD

The present invention relates generally to the field of machine learning and, more particularly, to identifying and visualizing relationships and commonalities amongst record entities.

BACKGROUND

Machine learning is a field of computer science that enables computers to learn from their experiences and the tasks that they perform. In general, two broad categories of machine learning exist. One such category is known as supervised learning. In supervised learning, a human (i.e., a "teacher") provides a computer with inputs and desired outputs. The computer learns by mapping the inputs to the outputs and deriving rules to describe the how the inputs are related to the outputs. Supervised learning includes semi-supervised learning, active learning, and reinforcement learning. Unsupervised learning is another broad category of machine learning. In unsupervised learning, a computer is provided with inputs and analyzes the information without human guidance. Goals of unsupervised learning can be to identify patterns within the data or identify "features" within the data. A "feature" can be a means of labeling or otherwise identifying related concepts within data.

SUMMARY

According to one embodiment of the present invention, a method for identifying and visualizing relationships and commonalities amongst record entities is provided. The method includes: extracting, by one or more computer processors, a plurality of entities from one or more records; associating, by the one or more computer processors, each entity of the plurality of extracted entities with a respective feature vector of a plurality of feature vectors within a vector space of a feature matrix, wherein the plurality of feature vectors are distributed within the vector space of the feature matrix based, at least in part, on semantic relationships amongst entities within a corpus; for each entity of the plurality of extracted entities, generating, by the one or more computer processors, multidimensional coordinates within a dimensionally-reduced vector space of the feature matrix based, at least in part, on the respective feature vector of each entity of the plurality of extracted entities; and identifying, by the one or more computer processors, one or more cells of a cellular presentation of the feature matrix such that each of the one or more identified cells represents one of more respective entities of the plurality of extracted entities, wherein: each cell of the cellular presentation represents a respective range of multidimensional coordinates within the dimensionally-reduced vector space of the feature matrix; and each cell of the cellular presentation represents one or more feature vectors of the plurality of feature vectors within the feature matrix.

According to another embodiment of the present invention, a computer program product for identifying and visualizing relationships and commonalities amongst record entities is provided. The computer program product comprises a computer readable storage medium and program instructions stored on the computer readable storage medium. The program instructions include: program instructions to extract a plurality of entities from one or more records; program instructions to associate each entity of the plurality of extracted entities with a respective feature vector of a plurality of feature vectors within a vector space of a feature matrix, wherein the plurality of feature vectors are distributed within the vector space of the feature matrix based, at least in part, on semantic relationships amongst entities within a corpus; program instructions to, for each entity of the plurality of extracted entities, generate multidimensional coordinates within a dimensionally-reduced vector space of the feature matrix based, at least in part, on the respective feature vector of each entity of the plurality of extracted entities; and program instructions to identify one or more cells of a cellular presentation of the feature matrix such that each of the one or more identified cells represents one of more respective entities of the plurality of extracted entities, wherein: each cell of the cellular presentation represents a respective range of multidimensional coordinates within the dimensionally-reduced vector space of the feature matrix; and each cell of the cellular presentation represents one or more feature vectors of the plurality of feature vectors within the feature matrix.

According to another embodiment of the present invention, a computer system for identifying and visualizing relationships and commonalities amongst record entities is provided. The computer system includes one or more computer processors, one or more computer readable storage media, and program instructions stored on the computer readable storage media for execution by at least one of the one or more processors. The program instructions include: program instructions to extract a plurality of entities from one or more records; program instructions to associate each entity of the plurality of extracted entities with a respective feature vector of a plurality of feature vectors within a vector space of a feature matrix, wherein the plurality of feature vectors are distributed within the vector space of the feature matrix based, at least in part, on semantic relationships amongst entities within a corpus; program instructions to, for each entity of the plurality of extracted entities, generate multidimensional coordinates within a dimensionally-reduced vector space of the feature matrix based, at least in part, on the respective feature vector of each entity of the plurality of extracted entities; and program instructions to identify one or more cells of a cellular presentation of the feature matrix such that each of the one or more identified cells represents one of more respective entities of the plurality of extracted entities, wherein: each cell of the cellular presentation represents a respective range of multidimensional coordinates within the dimensionally-reduced vector space of the feature matrix; and each cell of the cellular presentation represents one or more feature vectors of the plurality of feature vectors within the feature matrix.

BRIEF DESCRIPTION OF THE DRAWINGS

FIG. 4A is a cellular presentation of a pre-trained model that identifies a plurality of entities extracted from medical records relating to a specific subject, in accordance with an embodiment of the present invention.

FIG. 4B represents a reduced view of the cellular presentation of the pre-trained model depicted in FIG. 4A that facilities alteration of the granularity of information depicted via the cellular presentation, in accordance with an embodiment of the present invention.

FIG. 4C is a scaled view of the cellular presentation of the pre-trained model depicted in FIG. 4B that represents a reduction in the level of granularity by a factor of two, in accordance with an embodiment of the present invention.

FIG. 4D is a view of cells represented by a single cell of the cellular presentation of the pre-trained model depicted in FIG. 4C at a higher level of granularity, in accordance with an embodiment of the present invention.

DETAILED DESCRIPTION

Embodiments of the present invention recognize that electronic record-keeping often generates large volumes of heterogeneous data with respect to the subject(s) for which records are kept. It is often desirable, however, to consolidate and present these forms of heterogeneous data in a human-comprehensible way such that insights can be made with respect to the state of a particular subject. Embodiments of the present invention further recognize that a subject often belongs to one or more classes, and that it is often advantageous to compare the characteristics of the subject to other members of such classes to determine whether the characteristics of the subject are typical or atypical with respect to the other members of the classes. Embodiments of the present invention provide a system for identifying relationships and commonalities among the characteristics of a class of subjects, and with respect to a specific subject, visualize the characteristics of the subject such that the visualization can be compared to visualizations of the characteristics of other members of the class.

Embodiments of the present invention will now be described in detail with reference to the Figures. It is to be understood that these embodiments are described only for the purpose of illustration, and to help those skilled in the art to understand and implement the present invention, without suggesting any limitation as to the scope of the invention. The invention described herein can be implemented in various manners other than the ones explicitly described herein.

Figure 1:
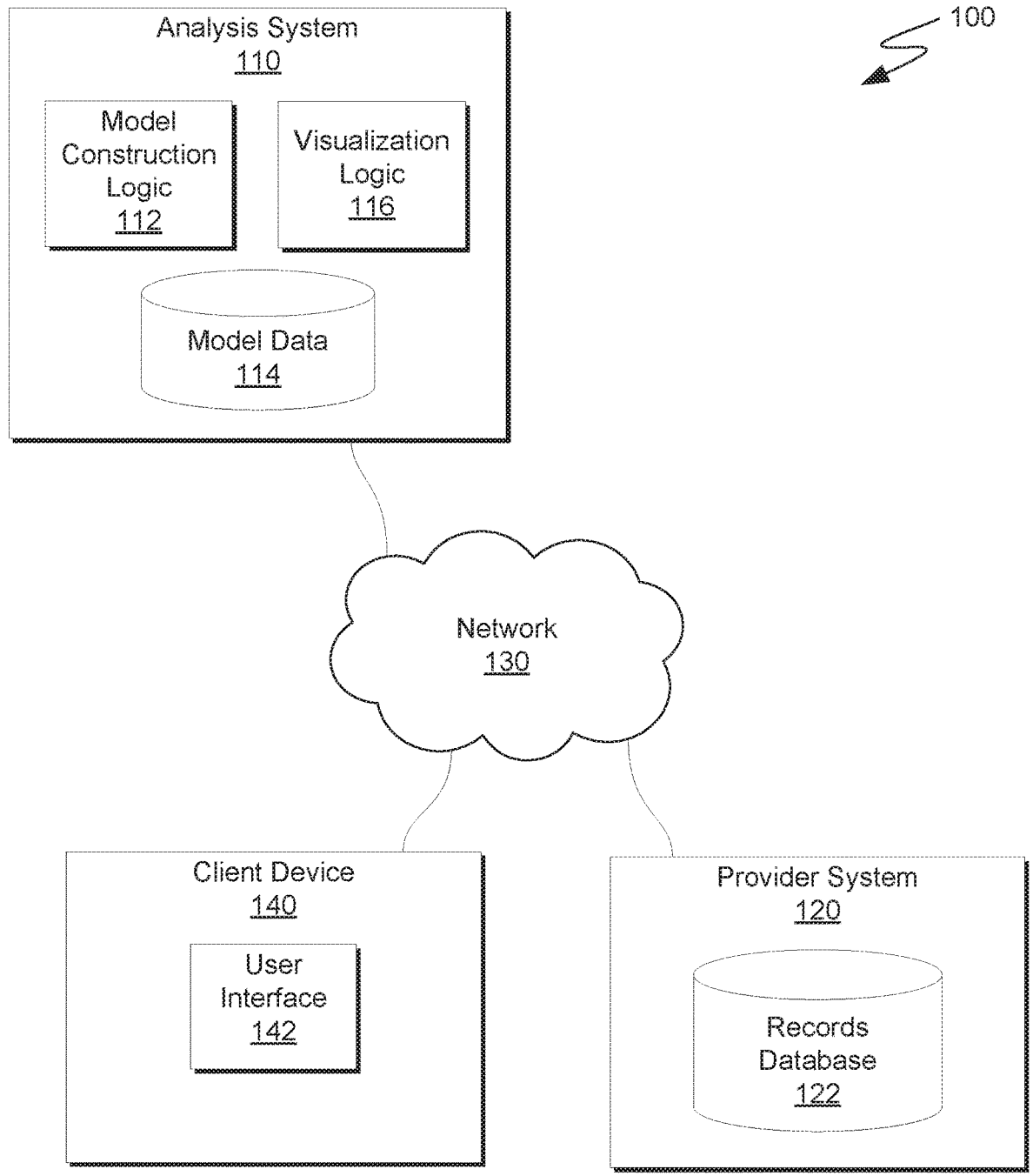
FIG. 1 is a functional block diagram illustrating a computing environment, in accordance with an embodiment of the present invention.

FIG. 1 is a functional block diagram illustrating a computing environment, in accordance with an embodiment of the present invention. For example, FIG. 1 is a functional block diagram illustrating computing environment 100. Computing environment 100 connects analysis system 110, provider system 120, and client device 140 via network 130. Analysis system 110 executes model construction logic 112 and visualization logic 116.

In various embodiments, analysis system 110 is a computing device that can be a standalone device, a server, a laptop computer, a tablet computer, a netbook computer, a personal computer (PC), or a desktop computer. In another embodiment, analysis represents a computing system utilizing clustered computers and components to act as a single pool of seamless resources. In general, analysis system 110 can be any computing device or a combination of devices with access to provider system 120 and client device 140, and with access to and/or capable of executing model construction logic 112 and visualization logic 116. In the embodiment depicted in FIG. 1, analysis system 110 stores model data 114 to facilitate execution of model construction logic 112 and visualization logic 116. Model data 114 represents a data repository that may be written to and read by one or both of model construction logic 112 and visualization logic 116. In general, model data 114 represents a repository including logic for extracting and relating characteristics of a plurality of subjects from structured and/or unstructured data in way that can be summarized and visualized using visualization logic 116. In some embodiments, model data 114 can be written to and read by programs and entities outside of computing environment 100 in order to populate the repository with data (e.g., a pre-trained model). Analysis system 110 may include internal and external hardware components, as depicted and described in further detail with respect to FIG. 6.

Additionally, in some embodiments, analysis system 110 represents a cloud computing platform that provides the functionality attributed to model construction logic 112 and/or visualization logic 116. Cloud computing is a model or service delivery for enabling convenient, on demand network access to a shared pool of configurable computing resources (e.g., networks, network bandwidth, servers, processing, memory, storage, applications, virtual machines, and services) that can be rapidly provisioned and released with minimal management effort or interaction with a provider of a service. A cloud model may include characteristics such as on-demand self-service, broad network access, resource pooling, rapid elasticity, and measured service; can be represented by service models including a platform as a service (PaaS) model, an infrastructure as a service (IaaS) model, and a software as a service (SaaS) model; and can be implemented as various deployment models including as a private cloud, a community cloud, a public cloud, and a hybrid cloud.

In the embodiment depicted in FIG. 1, model construction logic 112 and visualization logic 116 are stored on analysis system 110. In other embodiments, one or both of model construction logic 112 and visualization logic 116 reside on another computing device, provided that each can access and is accessible by each other, and provided that each can respectively access provider system 120 and client device 140, as described herein. In yet other embodiments, one or both of model construction logic 112 and visualization logic 116 are stored externally and accessed through a communication network, such as network 130. Network 130 can be, for example, a local area network (LAN), a wide area network (WAN) such as the Internet, or a combination of the two, and may include wired, wireless, fiber optic or any other connection known in the art. In general, network 130 can be any combination of connections and protocols that will support communications between analysis system 110 and provider system 120 and between analysis system 110 and client device 140, in accordance with a desired embodiment of the present invention.

Figure 2:
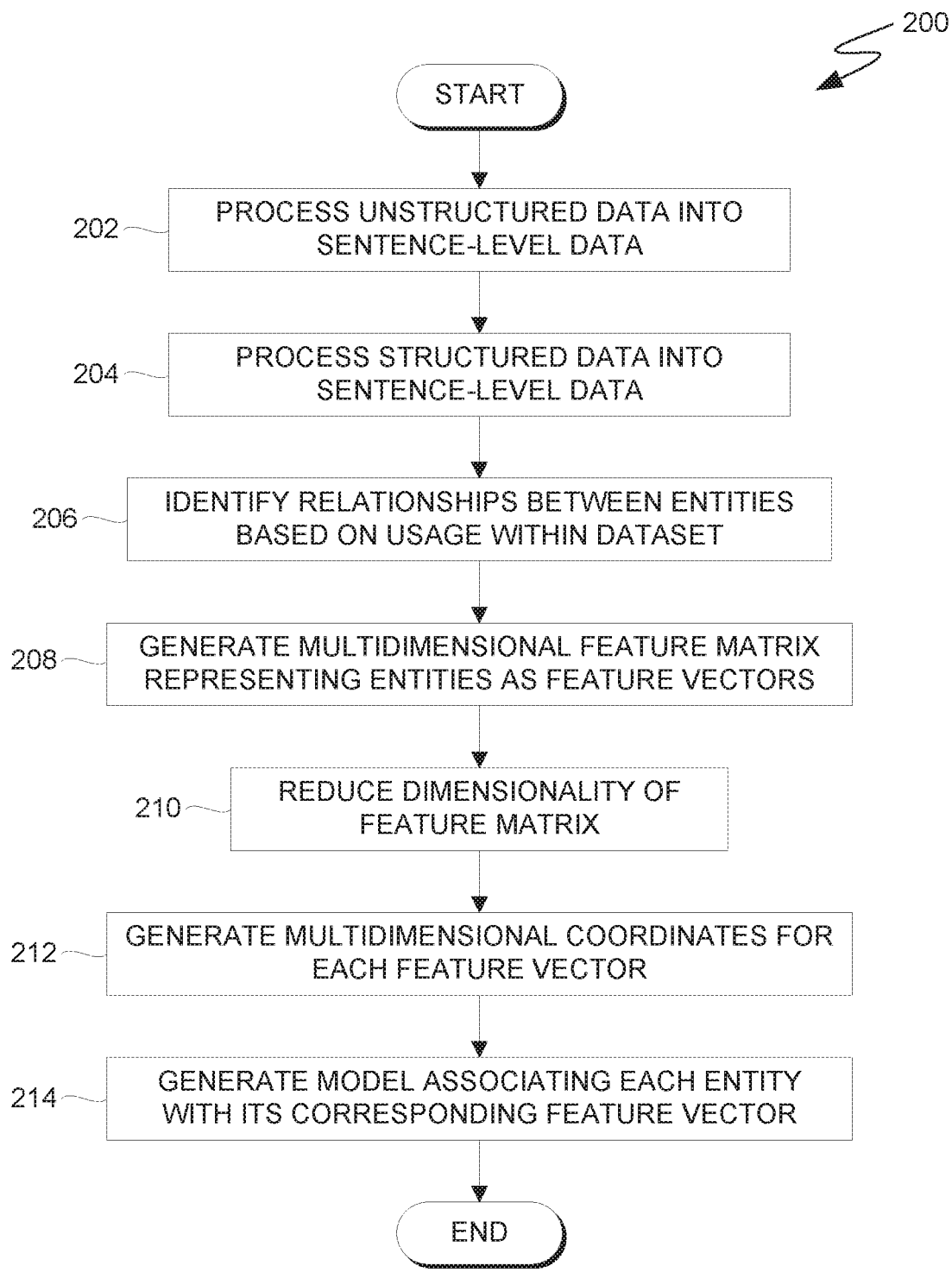
FIG. 2 is a flowchart depicting operations for constructing a model that represents sematic relationships amongst entities within a dataset, on a computing device within the computing environment of FIG. 1, in accordance with an embodiment of the present invention.
Figure 3:
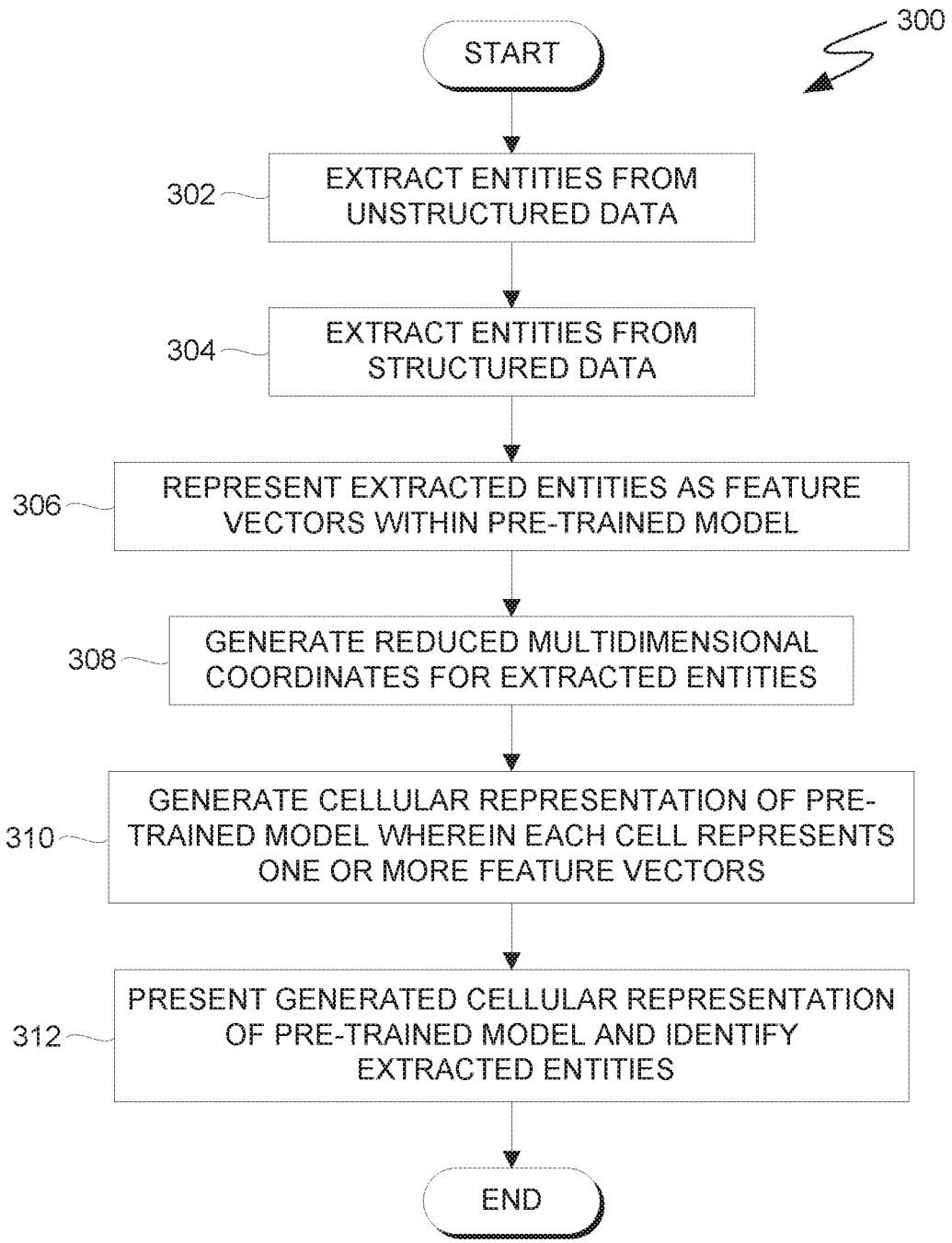
FIG. 3 is a flowchart depicting operations for visualizing information contained within a plurality of records using a pre-trained model, on a computing device within the computing environment of FIG. 1, in accordance with an embodiment of the present invention.

Model construction logic 112 is described in greater detail with respect to FIG. 2, and visualization logic 116 is described in greater detail with respect to FIG. 3. In general, model construction logic 112 operates to analyze data representing multiple subjects, extract characteristics (i.e., entities) that represent each subject, and construct model(s) that identify relationships between the characteristics of the subjects; visualization logic 116 operates to visualize characteristics of individual subjects based, at least in part, on the relationships between characteristics identified in the model(s) constructed by model construction logic 112. Is some embodiments, however, the pre-trained model is created, at least in part, from a corpus or corpora that can represent any subject (e.g., text books and scientific publications).

In various embodiments, provider system 120 is a computing device that can be a standalone device, a server, a laptop computer, a tablet computer, a netbook computer, a personal computer (PC), or a desktop computer. In another embodiment, provider system 120 represents a computing system utilizing clustered computers and components to act as a single pool of seamless resources. In general, provider system 120 can be any computing device or a combination of devices with access to, and that can be accessed by, analysis system 110 and that is capable of hosting, or otherwise providing, information within records database 122 to model construction logic 112 and/or visualization logic 116 of analysis system 110. In some embodiments, provider system 120 and analysis system 110 are controlled by separate entities (i.e., individuals and/or organizations). In other embodiments, provider system 120 and analysis system 110 are controlled by a common entity. In yet other embodiments, provider system 120 and analysis system 110 represent different logical and/or physical components of a common computer system. Provider system 120 can include internal and external hardware components, as depicted and described in further detail with respect to FIG. 6.

Records database 122 is a data repository that may be written to and read by one or both of model construction logic 112 and visualization logic 116. In general, records database 122 represents a repository including structured and/or unstructured data relating to a plurality of subjects that can be used by model construction logic 112 to construct a model that may enable information relating to the subjects and/or a new subject to be summarized and visualized using visualization logic 116. Stated differently, records database 122 represents, among other things, a corpus from which model construction logic 112 can construct model(s). In some embodiments, records database 122 can be written to and read by programs and entities outside of computing environment 100 in order to populate the repository with structured and/or unstructured data relating the plurality of subjects. Embodiments of the present invention are not limited to utilizing a single provider system, and various embodiments can use any number of instances of provider system 120 to provide model construction logic 112 with data to form a corpus from which a model can be constructed.

In various embodiments, client device 140 is a computing device that can be a standalone device, a server, a laptop computer, a tablet computer, a netbook computer, a personal computer (PC), personal digital assistant (PDA), a smart phone, or any programmable electronic device capable of communicating with analysis system 110 via network 130. In other embodiments, client device 140 represents a computing system utilizing clustered computers and components to act as a single pool of seamless resources. In general, client device 140 can be any computing device or a combination of devices with access to analysis system 110, and with access to and/or capable of executing visualization logic 116 and providing user interface 142. In some embodiments, client device 140 represents a "thick" client with respect to analysis system 110 (e.g., one or more logical components of model construction logic 112 and/or visualization logic 116 can execute locally on client device 140). In other embodiments, client device 140 represents a "thin" client with respect to analysis system 110 (e.g., client device 140 can receive the results of executing model construction logic 112 and/or visualization logic 116 on analysis system 110). Client device 140 can include internal and external hardware components, as depicted and described in further detail with respect to FIG. 6.

User interface 142 executes locally on client device 140 and operates to provide a user interface to a user of client device 140. User interface 142 further operates to receive user input from the user via the provided user interface, thereby enabling the user to interact with client device 140. For example, user interface 142 can provide a user interface that enables a user of client device 140 to interact with visualization logic 116 and/or model construction logic 112 via network 130. In various examples, the user interacts with visualization logic 116 via user interface 142 in order to view information analyzed using, at least in part, model construction logic 112 and/or visualization logic 116. In some embodiments, user interface 142 represents a user interface of analysis system 110 and there is no distinction between analysis system 110 and client device 140.

FIG. 2 is a flowchart depicting operations for constructing a model that represents sematic relationships between entities within a dataset, on a computing device within the computing environment of FIG. 1, in accordance with an embodiment of the present invention. For example, FIG. 2 is a flowchart depicting operations 200 of model construction logic 112 on analysis system 110 within computing environment 100.

Within computing environment 100, model construction logic 112 analyzes data corresponding to various records within records database 122 to identify relationships and commonalities therein. In various embodiments, records database 122 includes unstructured data and structured data. Model construction logic 112 utilizes various text segmentation techniques to process unstructured data into sentence-level data (operation 202) and process structured data into sentence-level data (operation 204). Some embodiments of model construction logic 112, however, are neither limited to utilizing a combination of structured and unstructured data nor limited to processing electronic records into sentence-level data. Some embodiments, for example, can process the structured and unstructured data into smaller parts, such as fragments (i.e., a window-size can be specified). In the case of structured data, model construction logic 112 can use a crawler or various other information extraction techniques known in the art to identify field labels within electronic forms and the values of respective field variables. In the case of unstructured data, model construction logic 112 can utilize various text segmentation techniques known in the art to divide unstructured data into constituent sentences or other linguistic units. Processing unstructured and structured data into sentence-level data is advantageous in that it can reduce the complexity of identifying relationships within the data (e.g., as opposed to analyzing paragraph-level data), while preserving, at least in part, information with respect to the usage of entities in the data. As used herein, "entities" represent respective pieces of information appearing in various electronic records.

In one specific example, embodiments of the present invention recognize that data relating to medical patients is often distributed amongst electronic medical records (EMR)

and unstructured, natural language records (e.g., physician notes). For example, it is recognized that it is not uncommon for a patient's file to contain ten, twenty, thirty, or more natural language notes and for patient data to be distributed amongst several EMR databases. With respect to structured EMR data, a patient's EMR data may include forms having predefined fields in which values for the patient are entered (e.g., fields for height, weight, blood type, etc.). Electronic forms can also have undefined fields (i.e., semi-structured records) in which nurses, physicians, and other medical personnel can enter information in natural-language form (e.g., fields to record notes and capture other information not associated with a particular field). In other cases, a record may consist solely of unstructured data (e.g., an electronically scanned image of a physical note or form). In some embodiments, model construction logic 112 incorporates optical character recognition to convert images of typed, handwritten, or printed text into machine-readable text for further processing.

In various embodiments, model construction logic 112 utilizes one or more unsupervised machine-learning algorithms to automatically identify semantic relationships between entities in the processed electronic record data (operation 206). In the context of medical records, for example, various diagnoses, symptoms, treatments, and outcomes can represent respective entities. FIGS. 4A-4D identify exemplary entities in the context of medical records. Model construction logic 112 can use algorithms such as Word2vec, GloVe, and various other word-embedding machine learning algorithms known in the art to identify semantic relationships between entities in the processed electronic record data (operation 206) and generate a multidimensional feature matrix (i.e., vector space) representing entities as respective feature vectors (operation 208). In general, word-embedding algorithms produce a large vector space from a corpus or corpora (e.g., the sentence-level data generated in operations 202 and 204) in which the each entity is assigned a corresponding feature vector. The feature vectors capture the context (i.e., usage) of entities within the dataset in that the feature vectors of entities are located within the vector space such that the proximity between feature vectors is proportional to the degree of commonality of their respective contexts within the dataset; additionally, techniques including vector addition and subtraction can be used to capture semantic and syntactic relationships between entities. Stated differently, entities that are semantically similar will have similar feature vectors and entities that are semantically dissimilar will have dissimilar feature vectors. In some embodiments, subsampling high frequency entities (i.e., words occurring above a threshold frequency) is advantageous because high frequency entities generally provide little contextual information and subsampling such entities can reduce the time and computational resources needed to generate the feature matrix.

The feature matrix that model construction logic 112 generates from the processed structured and/or unstructured data can be of very high dimensionality. Word-embedding algorithms, for example, generally produce a feature matrix in which each feature vector represents a dimension within the feature matrix. Feature matrices can include tens, hundreds, or thousands of feature vectors (e.g., 100-1000 feature vectors is typical). Accordingly, the resulting feature matrix can have tens, hundreds, or thousands of dimensions (e.g., 100-1000 dimensions). Embodiments of the present invention recognize that it is advantageous to reduce the dimensionality of the feature matrices to facilitate visualization of feature matrices in a human comprehensible way, as described herein. In the embodiment depicted in FIG. 2, model construction logic 112 reduces the dimensionality of the generated feature matrix (operation 210) using algorithms such as principal component analysis (PCA), t-distributed stochastic neighbor embedding (T-SNE), or other linear or non-linear dimensionality reduction algorithms known in the art. Reducing the dimensionality of the feature matrix yields a continuous vector space of lower dimension. In general, entities will form various clusters based, at least in part, on the semantic relationships amongst the entities.

To facilitate visualization of feature matrices in a human-comprehensible way, it is generally advantageous to reduce the dimensionality of the feature matrix to two or three dimensions, although reducing the feature matrix to other n-dimensional vector spaces is possible. For example, reducing the feature matrix to two dimensions enables each feature vector to be represented via a data point in a continuous two-coordinate system (i.e., a two-dimensional representation having an x-axis and a y-axis), and reducing the feature matrix to three dimensions enables each feature vector to be represented via a data point in a continuous three-coordinate system (e.g., a three-dimensional representation having an x-axis, a y-axis, and a z-axis). Model construction logic 112 generates multidimensional coordinates for each feature vector (operation 212) based on the product of the dimensionality reduction on the feature matrix (operation 210). Model construction logic 112 constructs a model (operation 214) for the processed structured and/or unstructured data by associating each entity with the multidimensional coordinates of the respective feature vector within the dimensionally-reduced feature matrix. In some embodiments, however, model construction logic 112 does not reduce the dimensionality of the feature matrix (i.e., operation 210 is omitted from operations 200) and the model associates each entity with a respective feature vector in the non-dimensionally-reduced feature matrix (i.e., the feature matrix generated via operation 208). Model construction logic 112 stores the constructed model as a pre-trained in model data 114. Visualization logic 116 can advantageously use the constructed model to visualize data within a specific subject's record(s) (e.g., the records of a specific medical patient), as described herein with respect to FIG. 3.

FIG. 3 is a flowchart depicting operations for visualizing information contained within a plurality of records using a pre-trained model, on a computing device within the computing environment of FIG. 1, in accordance with an embodiment of the present invention. For example, FIG. 3 is a flowchart depicting operations 300 of visualization logic 116 on analysis system 110 within computing environment 100.

As described herein with respect to FIG. 2, records database 122 includes structured and/or unstructured data in record(s) that are associated with various subjects. In general, visualization logic 116 operates to visualize information within the record(s) of a specific subject (i.e., a specific person, place, object, or organization) stored in records database 122 based on a pre-trained model stored in model data 114. As discussed previously, each pre-trained model associates a plurality of entities with respective feature vectors. Based on entities identified in a pre-trained model, visualization logic 116 extracts entities from unstructured data within the record(s) of a specific subject (operation 302) and extracts entities from structured data within the record(s) of the specific subject (operation 304). Visualization logic 116 can utilize various name-entity recognition and extraction techniques known in the art to extract entities identified within the pre-trained model from the subject's structured and unstructured data.

To represent the extracted entities as feature vectors within the pre-trained model (operation 306), visualization logic 116 identifies the feature vector associated with each extracted entity within the pre-trained model and associates the identified feature vectors with the respective extracted entities. In embodiments for which model construction logic 112 stores the pre-trained model in a dimensionally-reduced form, visualization logic 116 can generate reduced multidimensional coordinates for the extracted entities (operation 308) by obtaining the reduced multidimensional coordinates of respective feature vectors directly from the data representing the pre-trained model. This is advantageous in that fewer computational resources can be dedicated to executing visualization logic 116. In some embodiments, however, a user of client device 140 may, via user interface 142, request that visualization logic 116 visualize the entities associated with the specific subject in a form having lower dimensionality than the feature vectors of the pre-trained model. For example, model construction logic 112 may generate a pre-trained model in which the feature vectors are associated with coordinates in a three-dimensional space but a user of client device 140 requests a two-dimensional visualization. In such embodiments, visualization logic 116 performs further dimensionality reduction on the dimensionally-reduced feature vectors to model the extracted entities within a lower-dimensional feature matrix in accordance with the requested type of visualization (operation 308). Visualization logic 116 can utilize dimensionality reduction algorithms including PCA and T-SNE algorithms, as discussed above with respect to FIG. 2 and operations 200 of model construction logic 112, to perform the further dimensionality reduction.

In embodiments for which model construction logic 112 stores the pre-trained model in a non-dimensionally-reduced form, visualization logic 116 associates the extracted entities with respective non-dimensionally-reduced feature vectors and performs dimensionality reduction on the feature matrix, as discussed with respect to FIG. 2 and operations 200 of model construction logic 112, to generate reduced multidimensional coordinates for the extracted entities (operation 308).

To visualize the extracted entities based on the pre-trained model, visualization logic 116 (i) represents the pre-trained model (i.e., the feature vectors within the feature matrix), at least in part, by generating a multidimensional cellular presentation of the pre-trained model such that each cell represents a range of reduced multidimensional coordinates (i.e., a subspace of the dimensionally-reduced feature vector space) that include one or more feature vectors within the pre-trained model (operation 310) and (ii) visually identifies the cells that represent the feature vectors corresponding to the entities extracted from the record(s) associated with the specific subject (operation 312).

Embodiments of the present invention recognize that feature vectors representing semantically related entities will tend to cluster to varying degrees, and that the clusters, in general, represent broader, more abstract concepts and/or more generic categories that encompass the entities associated with the respective feature vectors. Embodiments of the present invention further recognize that the degree of clustering (i.e., the feature vector density of a cluster) for any one concept or category is based, at least in part, on a number of feature vectors that are semantically related to the concept or category and the degree to which the feature vectors are semantically related (i.e., the proximity of the feature vectors within a cluster to one another). It is therefore advantageous, if possible, that the cellular presentation includes one or more cells that represent concepts and/or categories that encompass a plurality of respective feature vectors within the pre-trained model (i.e., multi-feature-vector cells). In some embodiments, visualization logic 116 uses a threshold feature vector density and/or a threshold radius from a point within a cluster (e.g., a centroid of a cluster) to identify feature vectors to represent as respective concepts and/or categories within the cellular presentation of the feature matrix. Similarly, various embodiments of visualization logic 116 utilize a threshold feature vector density and/or a threshold radius from a point within a cluster (e.g., a centroid of a cluster) and/or a threshold number of feature vectors, among various other factors, to identify the ranges of reduced multidimensional coordinates that define respective cells. Additionally, visualization logic 116 generates the cellular presentation of the pre-trained model such that the arrangement of cells represents, at least in part, the proximity of respective clusters and/or feature vectors within the dimensionally-reduced feature vector space (i.e., the sematic relatedness of the entities, concepts, and/or categories of respective clusters and/or feature vectors).

Embodiments of the present invention, however, further recognize that some feature vectors may be sufficiently unrelated to any other feature vector within the pre-trained model that it is advantageous to represent such feature vectors within the cellular presentation of the pre-trained model as cells that represent a single, respective feature vector (i.e., single-feature-vector cells). Various embodiments of visualization logic 116 utilize a threshold feature vector density and/or a threshold distance from points within clusters of feature vectors (e.g., centroids of respective clusters) and/or a threshold distance from any other feature vector, among other factors, to identify feature vectors that can be represented by dedicated, single-feature-vector cells. In some embodiments, visualization logic 116 utilizes a threshold usage frequency to advantageously exclude feature vectors associated with infrequently used entities from dedicated, single-feature-vector cells in the cellular presentation of the pre-trained model.

In various embodiment, visualization logic 116 labels each cell of the generated cellular presentation of the pre-trained model based on the respective one or more feature vectors that each cell represents. In one example, one or more multi-feature-vector cell labels correspond to the entities associated with feature vectors that represent centroids of the feature vectors represented by respective cells. In another example, one or more multi-feature-vector cell labels identify most-frequently used entities associated with a feature vector amongst the respective feature vectors. In yet another example, one or more multi-feature-vector cell labels identify abstract concepts and/or more generic categories represented by the entities associated with the respective cells. And in some embodiments, one or more multi-feature-vector cell labels may be manually selected from among the entities associated with respective feature vectors and/or manually created based on the concepts and/or categories associated with respective feature vectors. In general, single-feature-vector cell labels correspond to the entity associated with the respective feature vectors.

In the context of computing environment 100, visualization logic 116 presents the generated cellular presentation of the pre-trained model and extracted entities (operation 312) by displaying, on user interface 142 of client device 140, the cellular presentation of the pre-trained model and visually identifying the cells that correspond to the entities extracted from the record(s) of the specific subject, as further described with respect to FIGS. 4A-4D. The cellular presentation is advantageous, at least in part, because the user of client device 140 can more quickly identify relevant information and/or compare information versus other methods of presenting the information (e.g., serially viewing a subject's individual records). Additionally, enabling individuals to quickly identify and/or compare relevant information with a subjects record(s) can advantageously reduce energy consumption of the electronic device presenting the visualization (e.g., energy consumption of user interface 142 of client device 140) at least in part, as a result of presenting the information for a shorter period of time compared to other methods of presenting the information (e.g., presenting the subject's records on user interface 142 one at a time).

FIGS. 4A-4D and 5 discuss a specific application of operations 200, as discussed with respect to FIG. 2, and operations 300, as discussed with respect to FIG. 3, to medical records. Embodiments of the present invention, however, are not to be construed as being limited thereto. For example, embodiments of the present invention can be applied to records in other fields such as logistical records and economic records amongst other types of records. Embodiments of the present invention represent improvements in the fields of science and/or practice represented by the type of records to which they are applied.

Embodiments of the present invention recognize that it is often necessary for a medical professional to view a large number of heterogeneous patient records to develop a comprehensive understanding of a patient's condition. Embodiments of the present invention further recognize that a medical professional may wish to identify whether or not a patient has a particular diagnosis, treatment, symptom, comorbidity, lifestyle, or outcome from among information contained with a large number of heterogeneous patient records (i.e., any factor(s) associated with the domain(s) in which the pre-trained model was created). Embodiments of the present invention yet further recognize that a medical professional may wish to compare any one of, or any combination of, a patient's diagnoses, treatments, symptoms, and outcomes to those of other patients and/or over time. In view of these recognized factors, embodiments of the present invention advantageously provide a system that facilitates the visualization of structured and/or unstructured medical data contained within a specific patient's medical records, as described with respect to FIG. 3, based on a pre-trained model that describes relationships and commonalities in structured and unstructured medical data contained with medical records, as described with respect to FIG. 2. The visualization provided by the system can advantageously enable medical professionals to quickly identify a patient's diagnoses, treatments, symptoms, and/or outcomes; identify specific variables of interest; and/or quickly compare the condition of the patient to the conditions of other patients. The specific exemplary embodiments of the present invention discussed with respect to FIGS. 4A-4D and 5 therefore represent improvements in medical science and medical practice.

FIG. 4A is a cellular presentation of a pre-trained model that identifies a plurality of entities extracted from record(s) relating to a specific subject, in accordance with an embodiment of the present invention. More specifically, FIG. 4A depicts cellular presentation 400 as displayed on user interface 142 of client device 140 within the context of computing environment 100.

Cellular presentation 400 depicts a two-dimensional, five-by-five cellular cellular matrix that identifies various examples of medical conditions, symptoms, and treatments included in a pre-trained model. Embodiments of the present invention, however, are not to be construed as being limited to the cellular matrix dimensions discussed herein. Each cell can represent one or more feature vectors within a pre-trained model generated from a corpus or corpora of medical records. For example, the cell labeled "sick" can represent feature vectors that are associated with the entities of "ill" and "disease" among others. In general, the arrangement of cells within cellular presentation 400 represents the semantic relatedness of the cells within the corpus or corpora (i.e., the semantic relatedness of the feature vector(s) represented by each cell), as described with respect to operations 300 of visualization logic 116. In the embodiment depicted in FIG. 4A, a subset of the cells is identified, via a hatch pattern, as cells that correspond to entities extracted from a specific patient's medical records, as described with respect to operations 300 of visualization logic 116, thereby enabling a medical professional to quickly identify the cells (i.e., the medical conditions, symptoms, and treatments) that describe the patient's condition. For example, a medical professional can determine that the specific patient represented by cellular presentation 400 is suffering from complications relating to Type 1 diabetes and is taking insulin.

In various embodiments, user interface 142 of client device 140 can identify the cells that correspond to the entities extracted from the specific patient's medical records via a difference in one of, or any combination of, color, opacity, framing, font, and font formatting, among other visual indicators, with respect to other cells in cellular presentation 400. Additionally, in some embodiments, a user can select the dimensions of the cellular presentation and/or select the identities of the cells presented within the cellular presentation via user interface 142 of client device 140.

FIG. 4B is a reduced view of the cellular presentation of the pre-trained model depicted in FIG. 4A that facilities alteration of the granularity of information depicted via the cellular presentation, in accordance with an embodiment of the present invention. More specifically, FIG. 4B depicts cellular presentation 410, which differs from cellular presentation 400 in that cellular presentation 410 is a two-dimensional, four-by-four cellular matrix instead of a two-dimensional, five-by-five cellular matrix.

Visualization logic 116 produces reduced cellular presentations, such as cellular presentation 410, at least in part, to facilitate alterations to the level of granularity at which visualization logic 116 depicts the cellular presentation of the pre-trained model. As used herein, a high level of granularity refers to a cellular presentation having a large number of cells and a low level of granularity refers to a cellular presentation having a smaller number of cells. Cellular presentations having a high level of granularity are advantageous at least in that such representations can communicate information with a high level of specificity but are disadvantageous in that it may be more difficult and/or take longer for persons to extract information that they seek. Cellular presentations having a low level of granularity are advantageous at least in that such representations can enable persons to extract information that they seek relatively quickly but are disadvantageous in that they communicate information with a lower level of specificity. It is therefore advantageous that a user has at least some control over the level of granularity at which visualization logic 116 presents the cellular presentations of pre-trained models. For example, user interface 142 of client device 140 can include a slider and/or or input field and/or register I/O device commands that enable a user to raise or lower the level of granularity.

Visualization logic 116 can produce cellular presentation 410 from cellular presentation 400 by omitting the left-most column of cells and the bottom row of cells from cellular presentation 400. Visualization logic can produce other two-dimensional, four-by-four cellular matrices from cellular presentation 400 by omitting other rows and columns. In some embodiments, user interface 142 of client device 140 enables a user of client device 140 to select the cells included in a reduced cellular visualization and/or omitted from the reduced cellular presentation. Reducing the cellular presentation to a four-by-four cellular matrix advantageously presents a reduced cellular presentation that enables the level of granularity to scale by factors of two. In other embodiments, visualization logic 116 can produce reduced cellular presentations that scale by other factors (e.g., a nine-by-nine cellular matrix from a ten-by-ten cellular matrix to facilitate scaling by a factor of three). In some embodiments, user interface 142 of client device 140 enables a user of client device 140 to select the scaling factor and/or select a scaling function. For example, selecting a scaling function via user interface 142 can cause visualization logic 116 to "snap" to a presentation of a reduced cellular matrix that can scale based on a selected scaling factor (e.g., "snap" to cellular presentation 410 from cellular presentation 400).

FIG. 4C is a scaled view of the cellular presentation of the pre-trained model depicted in FIG. 4B that represents a reduction in the level of granularity by a factor of two, in accordance with an embodiment of the present invention. More specifically, FIG. 4C depicts cellular presentation 420, which differs from cellular presentation 410 in that cellular presentation 420 is a two-dimensional, two-by-two cellular matrix instead of a two-dimensional, four-by-four cellular matrix.

While cellular presentation 420 depicts a plurality of cells at a level of granularity (i.e., four cells) that is a quarter that of cellular presentation 410 (i.e., sixteen cells), cellular presentation 420 preserves, at least in part, the information represented by cellular presentation 410. More specifically, cellular presentation 420 included cell 422, cell 424, cell 426, and cell 428. Cell 422 represents an upper left-hand quadrant of cellular presentation 410 (i.e., four cells), cell 424 represents an upper right-hand quadrant of cellular presentation 410 (i.e., four cells), cell 426 represents a lower left-hand quadrant of cellular presentation 410 (i.e., four cells), and cell 428 represents a lower right-hand quadrant of cellular presentation 410 (i.e., four cells). In the embodiment depicted in FIG. 4C, each of cell 422, 424, 426, and 428 is labeled with the labels of the respective cells of cellular presentation 410.

Within each cell of cellular presentation 420, visualization logic 116 identifies, utilizing a system of hatch patterns in the embodiment depicted in FIG. 4C, a number of cells from cellular presentation 410 (i.e., the non-reduced cellular presentation and/or the cellular presentation displayed immediately prior to the current cellular presentation) corresponding to the entities extracted from the patient's medical record(s). For example, a first hatch pattern in cell 426 indicates that all four cells represented by cell 426 of cellular presentation 410 correspond to entities extracted from the patient's medical record(s). Similarly, a second hatch pattern in cell 422 and a third hatch pattern in 424 indicate that cell 422 and cell 424 respectively correspond to three extracted entities and one extracted entity. A fourth hatch pattern (not shown) can indicate that a cell in cellular presentation 420 corresponds to two extracted entities. Cell 428 does not include any hatch pattern because the cells represented by cell 428 do not correspond with any extracted entity. In various other embodiments, one of, or any combination of, color, opacity, framing, font, and font formatting, among other visual indicators, can be used to identify numbers of cells corresponding to extracted entities.

FIG. 4D is a view of cells represented by a single cell of the cellular presentation of the pre-trained model depicted in FIG. 4C at a higher level of granularity, in accordance with an embodiment of the present invention. More specifically, FIG. 4D depicts a view of the cells of cellular presentation 410 represented by cell 424 of cellular presentation 420.

As previously stated, embodiments of the present invention recognize that cellular presentations at relatively low levels of granularity can by disadvantageous in that they generally communicate information with a low level of specificity. For example, cell 424 of cellular presentation 420 indicates that one cell of the four cells in cellular presentation 410 represented by cells 424 corresponds to at least one extracted entity. A medical professional however, cannot identify the specific cells in cellular presentation 410 based on the level of granularity of cellular presentation 420. Embodiments of the present invention advantageously provide the capability to select cells within a cellular presentation and view any cells represented by the selected cell at a higher level of granularity. In the context of computing environment 100, user interface 142 of client device 140 enables a user of client device 140 to select a cell within a cellular presentation (e.g., cell 424 of cellular presentation 420) and view any cells represented by the selected cell (e.g., the four cells representing the upper right-hand quadrant of cellular presentation 410), including cells identified as corresponding to one or more extracted entities (e.g., the cell labeled "polydipsia (Thirst)" that is represented by cell 424 of cellular presentation 420). The user of client device 140 (e.g., a medical professional) may therefore quickly and visually identify a group of related characteristics of interest from among a plurality of characteristics (e.g., the medical conditions represented by cell 424 from among those represented by cells 422, 424, 426, and 428) and may quickly and visually identify specific characteristic(s) of interest within the group via a cellular presentation of the group at a higher level of granularity (e.g., the cellular presentation of the cells of cellular presentation 410 corresponding to cell 424).

In some embodiments, a user of client device 140 can view the record(s) from which entities where extracted via user interface 142 by selecting cell(s) corresponding to extracted entities and selecting an option to display or otherwise retrieve the record(s) from records database 122. User interface 142 can also provide a capability to retrieve record(s) from records database 122 by searching for a patient's records using, for example, labels of the cells that correspond to extracted entities.

Figure 5:
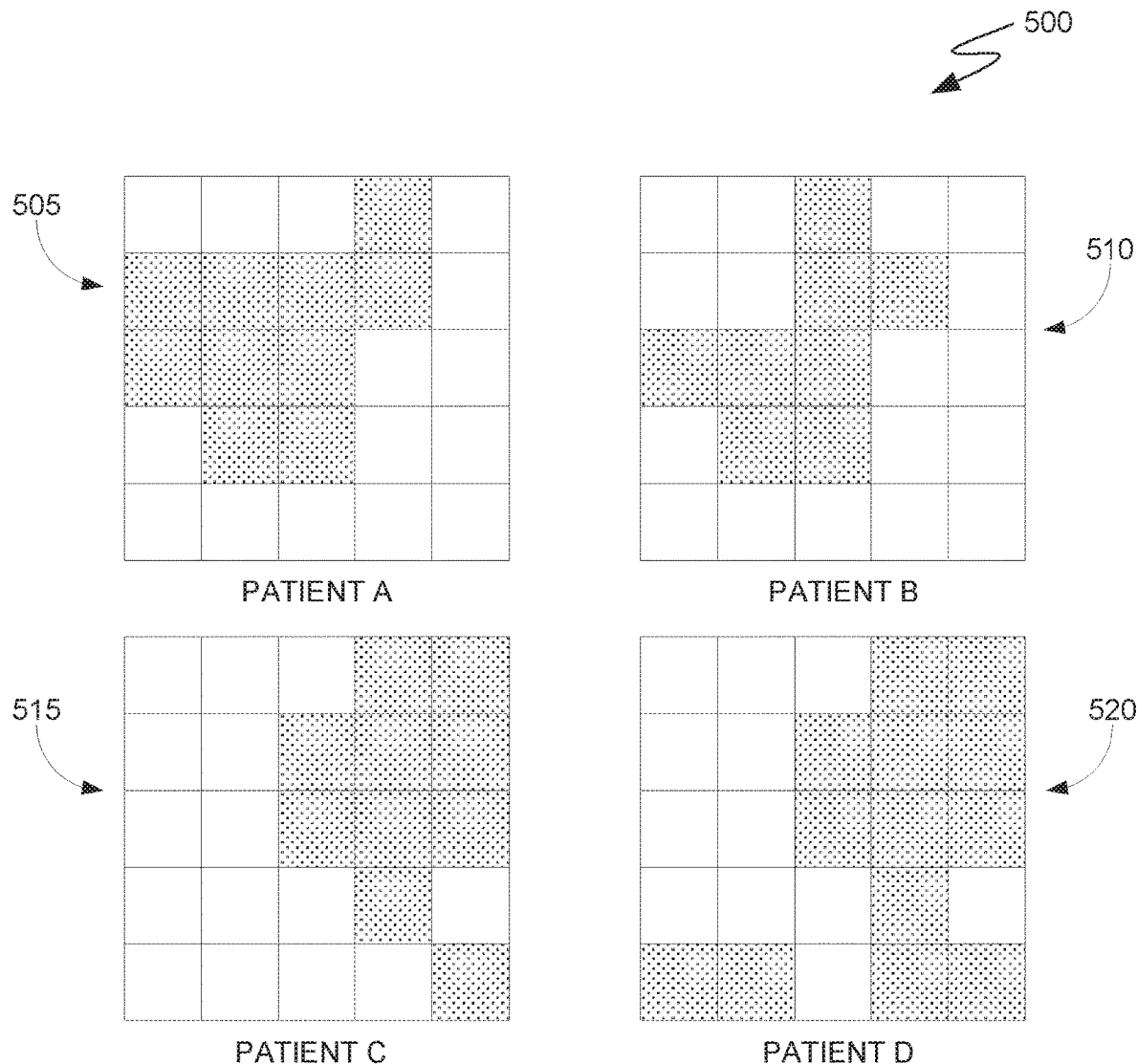
FIG. 5 is comparative view of a plurality of cellular presentations, as depicted in FIG. 4A, in accordance with an embodiment of the present invention.

FIG. 5 is comparative view of a plurality of cellular presentations, as depicted in FIG. 4A, in accordance with an embodiment of the present invention. More specifically, FIG. 5 depicts comparative view 500 that compares cellular presentation 505, cellular presentation 510, cellular presentation 515, and cellular presentation 520.

In the context of computing environment 100, comparative view 500 represents a feature of user interface 142 of client device 140 that enables a user of client device 140 to compare a plurality of cellular presentations of the pre-trained model and the cells corresponding to respective extracted entities. In the embodiment depicted in FIG. 5, cellular presentations 505, 510, 515, and 520 respectively correspond to "Patient A", "Patient B", "Patient C", and "Patient D" and each represents an instance of cellular presentation 400, as discussed with respect to FIG. 4A, that reflects the condition of the respective patient. A user of client device 140 (e.g., a medical professional) can advantageously use comparative view 500 to compare the diagnoses, symptoms, treatments, and/or outcomes of the various patients to identity relationships and commonalities among the conditions of the patients. In the embodiment, depicted in FIG. 5, cell labels are omitted from the instances of cellular presentation 400 to reduce visual clutter on user interface 142 in order to facilitate an easier comparison. In some embodiments, user interface 142 provides functionality that enables a user of client device 140 to toggle cell labels on and off. For example, a user may turn cell labels off while comparing instances of cellular presentation 400, and upon identifying one or more cells of interest, turn on cell labels to identify the corresponding characteristic of the patients.

Figure 6:
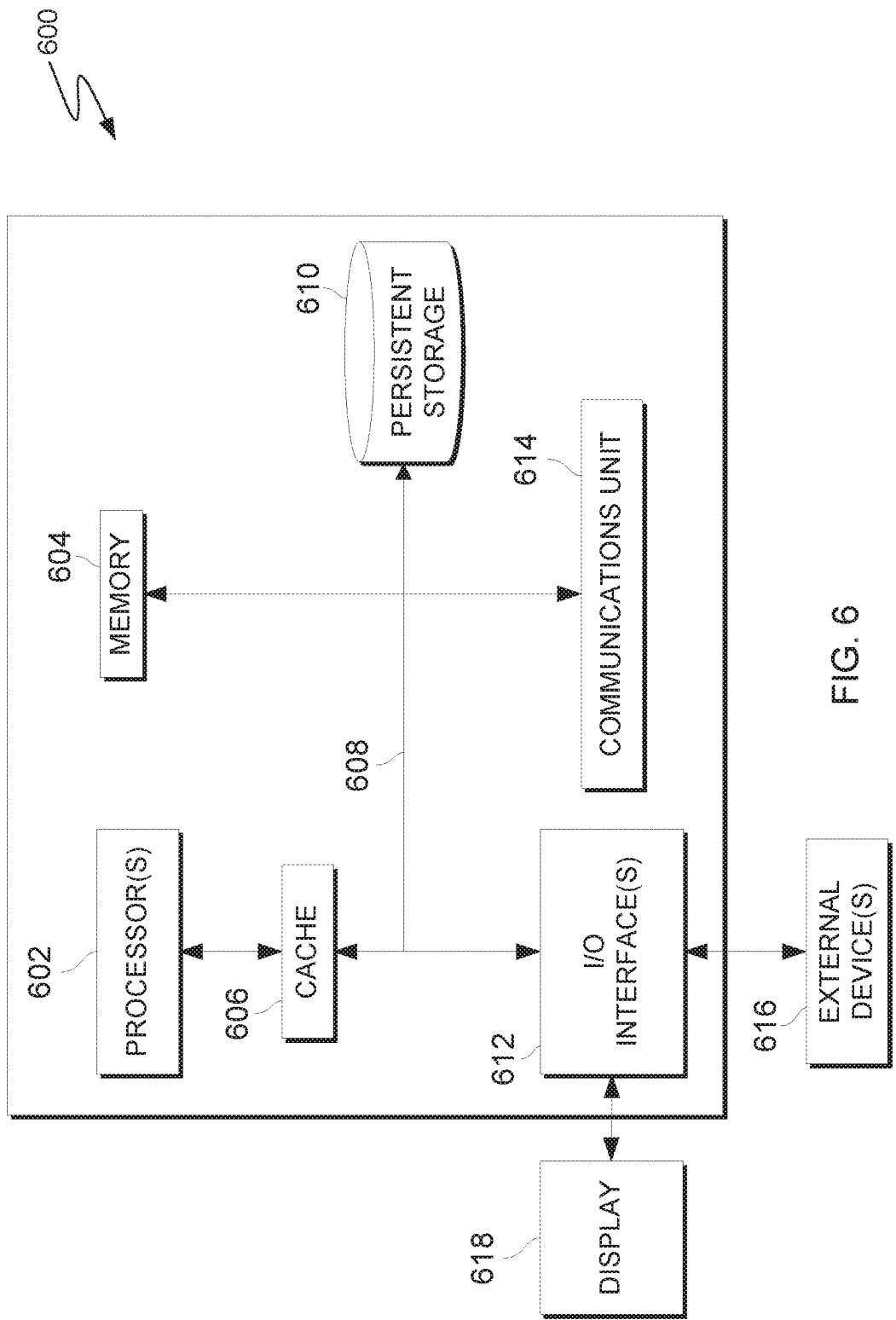
FIG. 6 is a block diagram of components of a computing device executing operations for identifying and visualizing relationships and commonalities among record entities, in accordance with an embodiment of the present invention.

FIG. 6 is a block diagram of components of a computing device executing operations for identifying and visualizing relationships and commonalities among record entities, in accordance with an embodiment of the present invention. In one embodiment, computing system 600 is representative of analysis system 110 within computing environment 100, in which case computing device 600 includes model construction logic 112 and visualization logic 116.

It should be appreciated that FIG. 6 provides only an illustration of one implementation and does not imply any limitations with regard to the environments in which different embodiments may be implemented. Many modifications to the depicted environment may be made.

Computing system 600 includes processor(s) 602, cache 606, memory 604, persistent storage 610, input/output (I/O) interface(s) 612, communications unit 614, and communications fabric 608. Communications fabric 608 provides communications between cache 606, memory 604, persistent storage 610, communications unit 614, and input/output (I/O) interface(s) 612. Communications fabric 608 can be implemented with any architecture designed for passing data and/or control information between processors (such as microprocessors, communications and network processors, etc.), system memory, peripheral devices, and any other hardware components within a system. For example, communications fabric 608 can be implemented with one or more buses or a crossbar switch.

Memory 604 and persistent storage 610 are computer readable storage media. In this embodiment, memory 604 includes random access memory (RAM). In general, memory 604 can include any suitable volatile or non-volatile computer readable storage media. Cache 606 is a fast memory that enhances the performance of processor(s) 602 by holding recently accessed data, and data near recently accessed data, from memory 604.

Program instructions and data used to practice embodiments of the present invention may be stored in persistent storage 610 and in memory 604 for execution by one or more of the respective processor(s) 602 via cache 606. In an embodiment, persistent storage 610 includes a magnetic hard disk drive. Alternatively, or in addition to a magnetic hard disk drive, persistent storage 610 can include a solid state hard drive, a semiconductor storage device, read-only memory (ROM), erasable programmable read-only memory (EPROM), flash memory, or any other computer readable storage media that is capable of storing program instructions or digital information.

The media used by persistent storage 610 may also be removable. For example, a removable hard drive may be used for persistent storage 610. Other examples include optical and magnetic disks, thumb drives, and smart cards that are inserted into a drive for transfer onto another computer readable storage medium that is also part of persistent storage 610.

Communications unit 614, in these examples, provides for communications with other data processing systems or devices. In these examples, communications unit 614 includes one or more network interface cards. Communications unit 614 may provide communications through the use of either or both physical and wireless communications links. Program instructions and data used to practice embodiments of the present invention may be downloaded to persistent storage 610 through communications unit 614.

I/O interface(s) 612 allows for input and output of data with other devices that may be connected to computer system 600. For example, I/O interface(s) 612 may provide a connection to external device(s) 616 such as a keyboard, keypad, a touch screen, and/or some other suitable input device. External device(s) 616 can also include portable computer readable storage media such as, for example, thumb drives, portable optical or magnetic disks, and memory cards. Software and data used to practice embodiments of the present invention can be stored on such portable computer readable storage media and can be loaded onto persistent storage 610 via I/O interface(s) 612. I/O interface(s) 612 also connect to display 618.

Display 618 provides a mechanism to display or present data to a user and may be, for example, a computer monitor.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As used herein, a list of alternatives such as "at least one of A, B, and C" should be interpreted to mean "at least one A, at least one B, at least one C, or any combination of A, B, and C."

Additionally, the phrase "based on" should be interpreted to mean "based, at least in part, on."

The term "exemplary" means of or relating to an example and should not be construed to indicate that any particular embodiment is preferred relative to any other embodiment.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A method for identifying and visualizing relationships and commonalities amongst record entities, the method comprising:

extracting, by one or more computer processors, a plurality of entities from one or more records;

associating, by the one or more computer processors, each entity of the plurality of extracted entities with a respective feature vector of a plurality of feature vectors within a vector space of a multidimensional feature matrix, wherein the plurality of feature vectors are distributed within the vector space of the multidimensional feature matrix based, at least in part, on using unsupervised learning to determine semantic relationships amongst entities within a corpus;

clustering, by the one or more computer processors, a number of feature vectors that represent a category of a plurality of categories of semantically related entities;

reducing, by the one or more computer processors, the multidimensional feature matrix to one of a two-dimensional feature matrix or a three-dimensional feature matrix;

generating, by the one or more computer processors, coordinates within a dimensionally-reduced vector space of the reduced multidimensional feature matrix based, at least in part, on the respective feature vector of each entity of the plurality of extracted entities;

identifying, by the one or more computer processors, a range of coordinates of one or more cells of a cellular presentation of one of the two-dimensional feature matrix or the three dimensional feature matrix, at least in part, using a threshold feature vector density, wherein the feature vector density is determined by the number of feature vectors in the cluster, and wherein each of the one or more identified cells of represents the number of feature vectors representing a category of a plurality of categories;

providing, by the one or more computer processors, the one or more cells of the cellular presentation as a cell matrix with a user selected dimensionality; and reducing, by the one or more computer processors, a dimensionality of the cell matrix, based, at least in part, on a user selection by reducing a number of rows and columns in the cell matrix, wherein each cell of the one or more cells have a same size, and wherein providing one or more visual indicators to identify a number of the one or more cells in a user selected cell of the cell matrix with the reduced dimensionality.

2. The method of claim 1, further comprising:
presenting on a user interface, by the one or more computer processors, the cellular presentation of one of the two-dimensional feature matrix or the three-dimensional feature matrix with the identified one or more cells within the cellular presentation.

3. The method of claim 1, further comprising:
reducing, by the one or more computer processors, a level of granularity of the cellular presentation of the multidimensional feature matrix based, at least in part, on a user selection made via the user interface.

4. The method of claim 1, wherein at least one cell of the cellular presentation of the feature matrix represents a respective category of information within the corpus.

5. The method of claim 1, wherein an arrangement of cells within the cellular presentation represents, at least in part, the semantic relationships amongst the entities within the corpus.

6. The method of claim 1, wherein the cellular presentation of the reduced multidimensional feature matrix is a two-dimensional cellular presentation.

7. The method of claim 1, the method further comprising:
further reducing, by the one or more computer processors, a dimensionality of the dimensionally-reduced vector space of the feature matrix based, at least in part, on a user selection made via a user interface.

8. The method of claim 1, wherein providing the one or more cells of the cellular presentation as a cell matrix with the user selected dimensionality further comprises:
providing, the one or more computer processors, a cell label for each of the one or more cells representing one or more categories of the plurality of categories represented by the one or more entities associated with the one or more cells represented by the cell label.

9. A computer program product for identifying and visualizing relationships and commonalities amongst record entities, the computer program product comprising:
a computer readable storage medium and program instructions stored on the computer readable storage medium, the program instructions comprising:
program instructions to extract a plurality of entities from one or more records;
program instructions to associate each entity of the plurality of extracted entities with a respective feature vector of a plurality of feature vectors within a vector space of a multidimensional feature matrix, wherein the plurality of feature vectors are distributed within the vector space of the multidimensional feature matrix based, at least in part, on using unsupervised learning to determine semantic relationships amongst entities within a corpus;
program instructions to cluster a number of feature vectors that represent a category of a plurality of categories of semantically related entities;
program instructions to reduce the multidimensional feature matrix to one of a two-dimensional feature matrix or a three-dimensional feature matrix;
program instructions to generating coordinates within a dimensionally reduced vector space of the feature matrix based, at least in part, on the respective feature vector of each entity of the plurality of extracted entities;
program instructions to use a threshold feature vector density to identify a range of coordinates of one or more cells of a cellular presentation of one of the two-dimensional feature matrix or the three-dimensional feature matrix, at least in part, using a threshold feature vector density, wherein the feature vector density is determined by the number of feature vectors in the cluster, and wherein each of the one or more identified cells of represents the number of feature vectors representing a category of a plurality of categories;
program instructions to provide the one or more cells of the cellular presentation as a cell matrix with a user selected dimensionality; and
program instructions to reduce a dimensionality of the cell matrix, based, at least in part, on a user selection by reducing a number of rows and columns in the cell matrix, wherein each cell of the one or more cells have a same size, and wherein providing one or more visual indicators to identify a number of the one or more cells in a user selected cell of the cell matrix with the reduced dimensionality.

10. The computer program product of claim 9, wherein an arrangement of the one or more cells within the cellular presentation represents, at least in part, the semantic relationships amongst the plurality of extracted entities within the corpus.

11. The computer program product of claim 9, the computer instructions further comprising:
program instructions to further reduce a level of granularity the multidimensional feature matrix based, at least in part, on a user selection made via a user interface.

12. The computer program product of claim 11, wherein to reduce the multidimensional feature matrix to the three-dimensional feature matrix and the further reduction of the dimensionality of the three-dimensional feature matrix generates, at least in part, the cellular presentation of the feature matrix as a two-dimensional cellular presentation.

13. A computer system for identifying and visualizing relationships and commonalities amongst record entities, the computer system comprising:
- one or more computer processors;
- one or more computer readable storage media;
- program instructions stored on the one or more computer readable storage media for execution by at least one of the one or more processors, the program instructions comprising:
  - program instructions to extract a plurality of entities from one or more records;
  - program instructions to associate each entity of the plurality of extracted entities with a respective feature vector of a plurality of feature vectors within a vector space of a multidimensional feature matrix, wherein the plurality of feature vectors are distributed within the vector space of the multidimensional feature matrix based, at least in part, on using unsupervised learning to determine semantic relationships amongst entities within a corpus;
  - program instructions to cluster a number of feature vectors that represent a category of a plurality of categories of semantically related entities;
  - program instructions to reduce the multidimensional feature matrix to one of a two-dimensional feature matrix or a three-dimensional feature matrix;
  - program instructions to generating coordinates within a dimensionally reduced vector space of the feature matrix based, at least in part, on the respective feature vector of each entity of the plurality of extracted entities;
  - program instructions to use a threshold feature vector density to identify a range of coordinates of one or more cells of a cellular presentation of one of the two-dimensional feature matrix or the three-dimensional feature matrix, at least in part, using a threshold feature vector density, wherein the feature vector density is determined by the number of feature vectors in the cluster, and wherein each of the one or more identified cells of represents the number of feature vectors representing a category of a plurality of categories;
  - program instructions to provide the one or more cells of the cellular presentation as a cell matrix with a user selected dimensionality; and
  - program instructions to reduce a dimensionality of the cell matrix, based, at least in part, on a user selection by reducing a number of rows and columns in the cell matrix, wherein each cell of the one or more cells have a same size, and wherein providing one or more visual indicators to identify a number of the one or more cells in a user selected cell of the cell matrix with the reduced dimensionality.

14. The computer system of claim 13, wherein the multidimensional feature matrix is a two-dimensional vector space and the cellular presentation of the feature matrix is a two-dimensional cellular presentation.

15. The computer system of claim 13, wherein an arrangement of the one or more cells within the cellular presentation represents, at least in part, the semantic relationships amongst the plurality of extracted entities within the corpus.

16. The computer system of claim 13, the computer instructions further comprising:
- program instructions to further reduce a dimensionality of the dimensionally-reduced vector space of the three-dimensional feature matrix are based, at least in part, on a user selection made via a user interface.

17. The computer system of claim 16, wherein the three-dimensional feature matrix and the further reduction of the dimensionality of the three-dimensional feature matrix generates, at least in part, the cellular presentation as a two-dimensional cellular presentation.

* * * * *